US010821210B2

(12) United States Patent
Roser

(10) Patent No.: US 10,821,210 B2
(45) Date of Patent: Nov. 3, 2020

(54) INJECTIONS

(71) Applicant: Stablepharma Limited, Somerset (GB)

(72) Inventor: Bruce Roser, Cambridge (GB)

(73) Assignee: STABLEPHARMA LTD, Bath (GB)

( * ) Notice: Subject to any disclaimer, the term of this patent is extended or adjusted under 35 U.S.C. 154(b) by 528 days.

(21) Appl. No.: 14/372,146

(22) PCT Filed: Jan. 28, 2013

(86) PCT No.: PCT/GB2013/050183
§ 371 (c)(1),
(2) Date: Jul. 14, 2014

(87) PCT Pub. No.: WO2013/110956
PCT Pub. Date: Aug. 1, 2013

(65) Prior Publication Data
US 2014/0350483 A1 Nov. 27, 2014

(30) Foreign Application Priority Data

Jan. 27, 2012 (GB) .................... 1201426.2

(51) Int. Cl.
A61L 31/16 (2006.01)
A61K 9/00 (2006.01)
(Continued)

(52) U.S. Cl.
CPC ............ *A61L 31/16* (2013.01); *A61K 9/0019* (2013.01); *A61K 9/122* (2013.01); *A61L 31/026* (2013.01);
(Continued)

(58) Field of Classification Search
CPC .... A61L 31/125; A61L 31/026; A61L 31/146; A61L 2300/438; A61M 5/3129; A61M 5/178; A61M 5/3145; A61M 5/3294; A61M 5/2066; A61M 5/284; A61M 5/1409; A61K 9/122; A61K 9/0019; A61K 51/1272
See application file for complete search history.

(56) References Cited

U.S. PATENT DOCUMENTS 4,891,319 A 1/1990 Roser
5,569,209 A * 10/1996 Roitman ............... A61J 1/2096
251/149.4
(Continued)

FOREIGN PATENT DOCUMENTS

EP 1449523 8/2004
EP 1452171 9/2004
(Continued)

OTHER PUBLICATIONS

International Search Report and Written Opinion dated May 16, 2013 for International application No. PCT/GB2013/050183.
(Continued)

*Primary Examiner* — Bhisma Mehta
*Assistant Examiner* — Hamza A Darb
(74) *Attorney, Agent, or Firm* — Adsero IP

(57) ABSTRACT

A syringe containing a compressible porous matrix, which compressible porous matrix has in it a pharmaceutical in a soluble glass, Methods of producing and using the syringe, and compressible porous matrix inserts for insertion into a syringe barrel are also provided.

23 Claims, 8 Drawing Sheets

(51) Int. Cl.
  *A61M 5/178* (2006.01)
  *A61K 9/12* (2006.01)
  *A61L 31/02* (2006.01)
  *A61L 31/12* (2006.01)
  *A61L 31/14* (2006.01)
  *A61M 5/31* (2006.01)

(52) U.S. Cl.
  CPC ........... *A61L 31/125* (2013.01); *A61L 31/146* (2013.01); *A61M 5/178* (2013.01); *A61M 5/3129* (2013.01); *A61L 2300/438* (2013.01); *A61M 5/3145* (2013.01)

(56) References Cited

U.S. PATENT DOCUMENTS

| | | | | |
|---|---|---|---|---|
| 5,722,955 | A | * | 3/1998 | Racz .................. A61M 5/31511 604/121 |
| 5,905,038 | A | * | 5/1999 | Parton .................. B01L 3/0275 422/419 |
| 5,955,448 | A | | 9/1999 | Colaco |
| 7,153,472 | B1 | | 12/2006 | Bronshtein |
| 2002/0121203 | A1 | * | 9/2002 | Cohn .................. B41K 1/44 101/333 |
| 2008/0294100 | A1 | * | 11/2008 | de Costa ............. A61K 9/0019 604/84 |
| 2010/0279274 | A1 | * | 11/2010 | Lloyd, Jr. ............ G01N 33/544 435/5 |
| 2012/0225011 | A1 | * | 9/2012 | Hyde .................... A61K 31/00 424/1.11 |

FOREIGN PATENT DOCUMENTS

| | | |
|---|---|---|
| GB | 2187191 | 9/1987 |
| GB | 2429646 | 3/2007 |
| WO | WO 87/00196 | 1/1987 |
| WO | WO 96/40077 | 12/1996 |
| WO | WO 99/27983 | 6/1999 |
| WO | WO 2007/057717 | 5/2007 |
| WO | WO 2011/042542 | 4/2011 |
| WO | WO 2011/098837 | 8/2011 |

OTHER PUBLICATIONS

United Kingdom Search Report dated May 9, 2012 for Great Britain Application No. GB1201426.2.
Green & Angell, 1989 J. Phys. Chem. 93:2880-2882, "Phase relations and vitrification in saccharide water solutions and the trehalose anamaly".
Jones, et al., 1997 Journal of Controlled Release 49(1):71-79, "Mucoadhesive, syringable drug delivery systems for controlled application of metronidazole to the periodontal pocket: In vitro release kinetics, syringeability, mechanical and mucoadhesive properties".
Sanchez, et al., 1989, Proc. Nat. Acad. Sci 86:481-485, "Recombinant system for overexpression of cholera toxin B subunit in *Vibrio cholera* as a basis for vaccine development".
Takashi, et al., 1990 Nature 344:873-875, "Induction of CD8 cytotoxic T cells by immunization with purified HIV-1 envelope protein in ISCOMs".
WHO, UNICEF, 2009, World Bank, "State of the world's vaccines and immunization" $3^{rd}$ ed., Geneva, World Health Organization.
Lloyd, et al., 1998, Genetic Engineering News, "Revolutionizing Immunizations".
Lloyd, 2000, World Health Organization, Geneva, in collaboration with Department of Vaccines and Biological UNICEF, "Technologies for vaccine delivery in the $21^{st}$ Century".
Lloyd and Aguado, 1998, WHO Publication, "Pre-Filled monodose Injection Devices: A safety standard for new vaccines, or a revolution in the delivery of immunizations?".
Aguado, et al., WHO Publication No. A59781, vol. 12, No. 2, 1998, "General Policy issues: injectable solid vaccines: a role in future immunization?", 3 pgs.

* cited by examiner

INJECTIONS

RELATED APPLICATIONS

This application is a 35 U.S.C. § 371 national phase application of PCT/GB2013/050183 (WO 2013/110956) filed on Jan. 28, 2013, entitled "Improved Injections", which application claims the benefit of Great Britain Application Serial No. 1201426.2, filed Jan. 27, 2012, which is incorporated herein by reference in its entirety.

INVENTION FIELD

The invention refers to methods for the parenteral injection of medicines. In particular, a hypodermic syringe, typically used in the administration of medicaments, in which drugs or vaccines are stabilised in a porous matrix contained in the barrel of the syringe.

BACKGROUND

The syringe has a long history. A type of syringe with a barrel and plunger was in use in Roman times. However, pharmaceuticals have only been routinely injected using the hypodermic needle and syringe since their invention around 160 years ago. Surprisingly, the appearance and basic design of the syringe has changed little in more than a century and a half since then. A series of refinements has led to the highly efficient standard disposable syringe of today which still works in the same way as the original device. Sixteen billion syringes are used annually. The enduring popularity indicates an impressive "fitness for purpose". However serious drawbacks do exist and are only tolerated because no effective solution to them has yet been devised.

The first drawback is that the standard syringe as supplied must be manually filled at the time of injection with a precisely aspirated dose of the pharmaceutical. This is usually done from a separately supplied vial containing the drug in solution. Apart from the cost and inconvenience of supplying the vial, this process sometimes leads to aspiration of an incorrect dose or even the incorrect drugs being filled from the wrong vial and injected.

A syringe that was supplied pre-filled with the correct dose already in it would be a cheaper and safer alternative. Several attempts have been made to develop and popularise such pre-filled syringes (WO96/40077, WO99/27983) but pre-filled syringes also suffer from serious drawbacks. Firstly, although an empty syringe can be stored indefinitely at room temperature, when pre-filled with more labile drugs, they need refrigerated storage. Because the standard plastic syringes are slightly permeable to water vapour they cannot be used to store drugs dissolved in water except for a short time. Otherwise the drug maybe damaged by over-concentration and the correctness of the dose becomes uncertain. Alternatively, glass syringes, which are impermeable to water vapour, can be used but they add to the cost of injections and also constitute a sharps hazard. Broken glass syringes may injure both the patient and the health worker.

Secondly, although the necessity of refrigerating most unstable drugs can be ameliorated by drying the drug (usually in conjunction with stabilising agents) the results are less than perfect. Drugs that are freeze-dried in ampoules are still refrigerated for prolonged storage and still need to be aspirated into the syringe after re-hydration. An alternative, drying drug solutions inside the syringe itself, can be employed. For effective usability, the dried drug must be in a finely divided form so as to dissolve immediately on rehydration. This dried form can be achieved by either freeze drying (WO99/27983) or vacuum foam drying (WO96/40077). These are difficult and expensive processes. Drugs freeze dried in this way are usually kept refrigerated for optimum stability. However, carefully formulated and processed vacuum foam drying can provide a room-temperature-storable, safe and convenient product. However there is a large variability in the degree of foam formation with many syringes failing to foam at all. The formidable manufacturing difficulties of achieving successful drying within the syringe containing the pharmaceutical in liquid form and the high costs have stifled uptake of the process. A further technical disadvantage is that dried products of this type still require several minutes to redissolve completely and are not suitable as immediately injectable formulations.

This problem is particularly acute in the vaccine industry since virtually all vaccines are unstable to some degree and are required to be held in refrigerated storage. This "cold chain", which must extend all the way from the factory to provincial depots, is unreliable and frequently breaks down. In 2008 $17 billion worth of vaccines were administered worldwide. Between 2006 and 2015 the cost of scaling up coverage and delivering new vaccines worldwide is expected to rise to $76 billion (WHO, UNICEF, World Bank. *Stale of the world's vaccines and immunization,* 3rd ed. Geneva, World Health Organization, (2009)). The World Health Organization (WHO) point out that this will not be possible using standard vaccine formats ("Revolutionizing Immunizations." Jodar L., Aguado T, Lloyd J and Lambert P-H. Genetic Engineering News Feb. 15 (1998)). The cost of the cold chain for the vaccine industry and for non-governmental health organizations running immunization campaigns is enormous. The WHO has estimated that just the maintenance cost of the cold chain is over $200 million annually. In addition, immunization campaigns may reach only those living-close to the last link of the cold chain. Because of breakdowns in correct temperature storage between 50 and 70% of all vaccines are damaged (PATH. Preventing Accidental Freezing in the Cold Chain: An Introduction to Cold Chain Freezing and Some Options for Reducing It (2003)). A most important requirement of any new process for stabilising and delivering vaccines is determined by the very large cost of world-wide vaccination efforts. The expensive technologies described above are of no practical use in most areas.

Vaccination campaigns require medically trained staff to ensure that the dose is correctly injected and shows no obvious signs of degradation. The need to reconstitute vials of some vaccines, such as measles, yellow fever and BCG, in the field is also a serious concern. Upon rehydration these vaccines become unstable again and cannot be stored. They must be injected promptly after reconstitution, which is often not possible in mass vaccination campaigns. Reconstitution must be done precisely to ensure correct dosage and it also introduces a potential source of contamination which has led to clinical disasters.

It is often necessary to give more than one vaccine at a session and if multivalent vaccines are not available due to the chemical incompatibility of some of the components this may require 2 or more injections. The WHO has highlighted these problems by actively encouraging research into the next generation of stable multivalent vaccines which are presented in single injections and have no need for refrigeration (J. Lloyd. Technologies for vaccine delivery in the 21st century. *World Health Organization Geneva* (2000) *in collaboration with Department Of Vaccines And Biologicals UNICEF.,* Lloyd J. and Aguado M. T. Pre-Filled monadose Injection Devices: A safety standard for new vaccines, or a revolution in the delivery of immunizations? WHO publication May (1998). Aguado M T., Jodar L., Lloyd J., Lambert P. H. General Policy issues: injectable solid vaccines: a role in future immunization?" WHO publication No A59781).

INVENTION SUMMARY

To address the problems described above this invention proposes a conventional pharmaceutical syringe comprising a pharmaceutical material stabilised in a soluble dry glass coating the surfaces of the voids in a compressible porous matrix which is located within the barrel of the syringe between the plunger and the needle fitting.

Upon drawing the water into the syringe the soluble glass rapidly dissolves to release the pharmaceutical material into the water for injection. Compression of the porous matrix at the end of the injection stroke ensures delivery of the complete dose of vaccine.

Accordingly, the syringe of the present invention is suitable for the administration of a liquid-carried pharmaceutical to a patient. The syringe contains a pharmaceutical stabilized in a glass that is soluble in a carrier liquid (e.g. water, saline) and that is in a compressible porous matrix located in the barrel of the syringe, so that the glass dissolves in the carrier liquid thereby releasing the pharmaceutical into the carrier liquid for administration to the patient.

A wide range of bioactive molecules may be stabilized by drying in soluble glasses, particularly sugar glasses (see e.g., U.S. Pat. No. 4,891,319, GB2187191, U.S. Pat. No. 5,955, 448). These dry, stabilized actives are unaffected by high or freezing temperatures The mechanism underlying the remarkable stabilization of molecules by certain sugars is the ability of drying solutions to undergo glass-transformation rather than crystallisation. The disaccharide trehalose readily forms stable glasses (Green J L. & Angel C A. Phase relations and vitrification in saccharide water solutions and the trehalose anomaly J Phys. Chem. 93 2880-2882 (1989)) and has excellent stabilising properties.

One of the advantages of the present invention is that the compressible porous matrix having the pharmaceutical-containing glass in it can be dried outside the syringe and then inserted it into the syringe during the manufacturing step in a form that can easily and cheaply be manufactured and stored at ambient temperature without deterioration, and can be used immediately without any set up. The drying can be achieved by air drying, which is a convenient and low cost way of drying the glass that contains the pharmaceutical.

The provision of stable, ready-to-inject dose formulations that are relatively inexpensive and packed in the syringe itself greatly reduces costs since the additional storage and delivery costs for other equipment are saved. This is a particular advantage with multiple component formulations containing more than one active ingredient, such as multi-valent vaccines. Difficulties with chemical incompatibility of multiple components are reduced since they are stored in a dry, stable form. Further, the need for providing multiple phials containing the various active ingredients is avoided.

The invention is further defined in the annexed statements of invention and in the claims.

In a first aspect, the invention provides a syringe comprising a pharmaceutical in a soluble glass, wherein the soluble glass is in a compressible porous matrix. In a second aspect, the invention provides a compressible porous matrix insert comprising a pharmaceutical in a soluble glass, which insert is suitable for insertion into the barrel of a syringe.

In relation to the first aspect, the invention provides a pharmaceutical syringe, comprising a syringe barrel, and having a compressible porous matrix in the syringe barrel, wherein the compressible porous matrix has in it a pharmaceutical in a soluble glass.

In relation to the second aspect, the invention provides a compressible porous matrix insert, which is a body of a compressible porous matrix having in it a pharmaceutical in a soluble glass, which insert is suitable for inserting into the barrel of a syringe for delivery of the pharmaceutical to a subject.

Preferred or optional features of the invention will now be set out. These may be applied singly or in any combination with any aspect or development of the invention described herein, unless the context demands otherwise.

The term syringe refers to a pharmaceutical syringe, which is a syringe suitable for delivery of a pharmaceutical to a subject, particularly parenteral delivery of a pharmaceutical to a subject (a subject may also be referred to herein as a patient). The term syringe used herein encompasses any pharmaceutical injection device, for example a device used for mass inoculations. A syringe typically comprises a barrel, which is a compartment for holding or receiving a liquid for injection, and a plunger for actuating discharging of the liquid from the barrel for delivery of the liquid to a subject. The plunger may be fitted into one end of the barrel, while the other end of the barrel has an outlet connected to, or connectable to, a needle (e.g. a hypodermic needle) or a tubing or further medical apparatus. A syringe plunger typically has a sealing member at one end, which fits tightly into the syringe barrel to form a water-tight seal. The sealing member is also referred to herein as a seal. In use, depression of the plunger into the barrel drives fluid (air and/or liquid) from the barrel, out of the outlet at the needle end of the syringe, whereas outward drawing of the plunger draws fluid into the barrel, in through the needle end of the syringe. The drawing of fluid in to a syringe may be referred to as aspiration. The driving of fluid out of the syringe may be referred to as expelling or discharging or, in the context of delivery of fluid to a patient, injecting.

Before the syringe of the present invention is used for the delivery of a pharmaceutical to a subject, it is in a stored state. The syringe in its stored state may have the plunger at least partially in the barrel, or the plunger may be outside the barrel. The plunger may be packaged separately from the barrel. In its stored state the needle end of the syringe may be connected or attached to a needle, or the needle may be supplied separately in which case there is no needle connected or attached to the needle end of the syringe. The syringe in its stored state may contain the compressible porous matrix inside the barrel and/or the matrix may be attached to the seal of the plunger. The syringe in its stored state is typically stored in air and has air in the barrel. In its stored state there is no carrier liquid in the syringe barrel. The syringe may be provided in its stored state in a sterile and/or vacuum packed packaging.

Porosity is the fraction of voids in a material. If the porosity of a material is $\phi$, then its density, $\rho$, is related to $\phi$ by $\phi=(\rho_0-\rho)/\rho_0$ where $\rho_0$ is the pore-free density. Porosity can be expressed has a value between 0-1 or as a percentage between 0-100% where in the percentage indicates the void fraction in the material. Porous matrices suitable for use in the present invention may have porosities of up to about 70%, up to about 80%, up to about 85%, up to about 90%, up to about 95% or up to about 98%. Porous matrices suitable for use in the present invention may have porosities of at least about 50%, at least about 60%, at least about 70%, at least about 80%, at least about 90% or at least about 95%. Porous matrices suitable for use in the invention may have porosities of about 40-95%, about 50-95%, about 60-95%, about 70-95% or about 80-95%.

The porous matrices of the present invention preferably have a pore size of between about 1 micron and about 2 mm, between about 10 micron and about 1 mm, or between about 10 micron and about 100 micron. The pore size refers to the mean pore diameter The specific surface area of a porous matrix such as a foam is the amount of surface area within a given volume or mass of foam. The porous matrices for use in the present invention provide a large surface area on which a solution of a glass-forming material may be dried to provide a matrix with a glass in it. The porous matrices of the invention preferably have a high specific surface area. The porous matrices of the invention preferably have a specific surface area of about 0.1-100 $m^2/g$, about 1-100 $m^2/g$, about 5-100 $m^2/g$, about 10-100 $m^2/g$, about 0.1-20 $m^2/g$, about 1-20 $m^2/g$, about 5-20 $m^2/g$, about 10-20 $m^2/g$, about 10-50 $m^2/g$, about 10-500 $m^2/g$, about 50-500 $m^2/g$, at least about 0.1 $m^2/g$, at least about 1 $m^2/g$, at least about 10 $m^2/g$, or about 10 $m^2/g$ or about 20 $m^2/g$.

A compressible material accepts reduction in volume by applied pressure to form a compact. A compressible material or product may also be termed a compliant material or product. Compressibility in the context of the present invention can be measured and/or expressed as the ratio of the original non-compressed volume to the volume of the compressed compact. A compressible matrix for use in the present invention may have compressibility of about 5:1 or more, meaning that its volume in its non-compressed state is about five times or more greater than its volume in its compressed state, A compressible matrix for use in the present invention may have a compressibility of about 2:1 or more, about 3:1 or more, about 4:1 or more, about 5:1 or more, about 10:1 or more, about 20:1 or more, or about 50:1 or more.

A compressible porous matrix may be a solid foam body, which is a body comprising pockets or cells of gas in a solid. The foam is preferably open cell foam, i.e. a foam in which some, or most of, the gas pockets or cells connect with each other and to the outside of the foam body. Pockets or cells of a porous matrix may also be referred to as voids. Preferred foams are cellulose foams, melamine foams and hydrophilic reticulated polyether foams. The porous matrix may be formed from cellulose, polyethylene, polypropylene, polyester, polyether polyurethane, polyurethane, polyvinyl acetate, melamine formaldehyde resin or natural sponge.

The compressible porous matrix is preferably insoluble. That is, the compressible porous matrix is insoluble in a carrier liquid (e.g. water, saline), specifically, it is insoluble in the carrier liquid that is to be used to deliver the pharmaceutical to the subject. Preferably the compressible porous matrix is insoluble in water.

A compressible porous matrix may be in the form of a block, a cylinder, or a prism, optionally an elongate block, cylinder or prism, which may have a circular or a non-circular (e.g. rectangular) cross section. A matrix in the form of an elongate block may be inserted, or contained in, a syringe barrel such that the elongate block is lengthways along the longitudinal axis of the syringe barrel. A compressible porous matrix may also be referred to as a compressible porous supporting structure.

A glass is a non-crystalline solid. In particular, a glass is a hard, brittle non-crystalline solid. Glasses are amorphous solids, meaning that their structure lacks the regularity of crystalline solids. Glasses may be defined as those noncrystalline solids which exhibit a transition in behaviour (the glass transition) with temperature. The term "glass" herein refers to any glassy material or glassy substance, that is, any non-crystalline or amorphous solid. In particular, the term glass herein relates to organic glass, and refers to any solid formed from an organic glass-forming material. A glass suitable for use in the present invention is a soluble glass.

Glass-forming materials include amino acids, sugars, sugar alcohols, carbohydrates, carbohydrate derivatives and polyols (including carbohydrate and non-carbohydrate polyols) as described herein. The glass-forming material may be any non-reactive glass-forming sugar such as trehalose, raffinose or sucrose or mixtures of sugars or any other carbohydrate glass-former. Glass-forming materials are also referred to herein as stabilisers, stabilising excipients, or preservatives, because a pharmaceutical may be stored in the glass formed from the glass forming material without substantial losses in activity by denaturation, aggregation or other mechanisms.

A glass may be produced by preparing a solution of a glass-forming material in a solvent, which solution may be referred to as a preservative solution or a stabiliser solution. For example a solution comprising about 5-50% w/v, about 10-30% w/v, or about 10-50% w/v glass-forming material, or a solution comprising about 5%, about 7.5%, about 10%, about 15%, about 20%, about 25%, about 30%, about 35%, about 40%, about 45% or about 50% w/v glass-forming material. The glass-forming material may be trehalose. The glass for use in the present invention is prepared by drying a solution of glass-forming material, for example by air drying. The glass-forming material in the glass-forming solution vitrifies upon drying. In particular, the glass of the present invention may be prepared by preparing a solution of 10-30% w/v trehalose and drying the solution, preferably by air drying. In the preparation of glasses for use in embodiments of the invention, a pharmaceutical is also included in the glass-forming solution. Upon drying of the glass-forming solution, the pharmaceutical is stabilised in the glass. Such a glass may be referred to as a pharmaceutical-containing glass.

A compressible porous matrix may have in it a glass comprising a pharmaceutical. A porous matrix provides a large surface area on which a glass-forming solution can be dried. The surface of the matrix comprises the external surfaces of the matrix and the internal surfaces which are formed by the pore-forming pockets, cells, or voids or the matrix. Upon drying, the glass-forming solution forms a glass in the porous matrix; in this context, a glass in the porous matrix is a glass on at least some of the internal surfaces of the matrix, i.e. the surfaces formed by the pore-forming pockets, cells, or voids of the matrix. The internal surfaces of the matrix are thus coated with glass. The matrix may be referred to as coated with glass, or impregnated with glass.

The pharmaceutical in the glass is preferably stabilised in the glass. Such a pharmaceutical may be termed herein a glass stabilised pharmaceutical, a stabilised pharmaceutical, or a stable pharmaceutical in a glass. The term stable or stabilised refers to a substance, such as a pharmaceutical, which essentially retains its physical and chemical stability and integrity upon storage. In particular a stable or stabilised substance is a pharmaceutical (such as a therapeutic protein or a vaccine) that retains its activity, for example its biological or therapeutic activity, upon storage. Various analytical techniques for measuring stability of proteins are known and are reviewed in Jones, A. Adv. Drug Delivery Rev. 10:29-90 (1993). Stability and/or activity can be measured following storage at a selected temperature for a selected time period. Biological or therapeutic activity may be measured for example as enzymatic activity, binding activity (e.g. binding of an antibody to its antigen) or ability to elicit a specific result or response in vitro or in vivo.

The stable or stabilised pharmaceutical of the invention may be one which retains at least about 30%, at least about 40%, at least about 50%, at least about 60%, at least about 70%, at least about 80%, at least about 90%, at least about 95%, at least about 98% or at least about 99% activity following storage for a period of up to 1, 2, 3, 4, 5, 6, or 7 days or up to 2, 4, 8, or 12 weeks, or up to 1, 2, 3, 4, 6, 8, 12, 24 or 36 months at a temperature of between 10-60° C., 10-50° C., 10-40° C., 20-50° C., 20.40° C., or at about 18° C., 20° C., 25° C., 37° C., 45° C., 50° C., 60° C., or 70° C. For example, a stable or stabilised pharmaceutical the invention may be one which retains at least about 80% activity following storage for 2, 4, 8 or 12 weeks at 37° C., or may be one which retains at least about 80% activity following storage for about 2, 4, 8 or 12 weeks at 45° C. Percentage activity refers to the activity of the pharmaceutical after storage as a percentage of the activity of the same pharmaceutical in fresh (non-stored) form.

The term "soluble" refers to a substance that is capable of being dissolved in or as if in a fluid. The term soluble herein may refer to a substance, such as a glass, that is soluble in a solvent such as water and/or an aqueous solvent such as physiological saline. In the context of the present invention such a solvent may be termed a carrier liquid. The term soluble may refer to a substance, such as a glass, that is soluble in oil and/or an organic solvent. In the context of the present invention a soluble glass is preferably soluble in water.

Conversely the term "insoluble" refers to a substance that is not capable of being dissolved in a fluid. The term insoluble herein may refer to a compressible porous matrix that is insoluble in a solvent such as water and/or an aqueous solvent such as physiological saline. In the context of the present invention such a solvent may be termed a carrier liquid. The term insoluble may refer to a compressible porous matrix that is insoluble in oil and/or an organic solvent. In the context of the present invention a compressible porous matrix is preferably insoluble in water.

Preferably, a soluble glass is a dry soluble glass. The term "dry" refers to a glass having a residual moisture content of about 0.1-10% w/w, 0.1-5% w/w, about 0.1-2.5% w/w, about 0.1-1% w/w, about 0.05-1% w/w, about 0.1% w/w, about 0.5% w/w, about 1% w/w, about 2.5% w/w, about 5% w/w, or about 10% w/w.

The term "pharmaceutical" refers to any pharmaceutical material, pharmaceutical agent, or pharmaceutical product, including therapeutic agents, drugs, and prophylactic agents such as vaccines. The pharmaceutical may be any bioactive substance. Pharmaceuticals include vaccines, anti-inflammatory drugs, analgesics, antiarthritic drugs, antispasmodics, antidepressants, antipsychotics, tranquillisers, antianxiety drugs, narcotic antagonists, antiparkinsonism agents, cholinergic agonists, chemotherapeutic drugs, immunosuppressive agents, antiviral agents, antimicrobial agents, appetite suppressants, anticholinergics, antiemetics, antihistaminics, antimigraine agents, coronary, cerebral or peripheral vasodilators, hormonal agents, contraceptives, antithrombotic agents, diuretics, antihypertensive agents, cardiovascular drugs, opioids, and the like.

Pharmaceuticals may be any type of substance, Such substances include, but are not limited to, subcellular compositions, cells, bacteria, viruses and molecules including, but not limited to, lipids, organics, proteins and peptides (synthetic and natural), peptide mimetics, hormones (peptide, steroid and corticosteroid), D and L amino acid polymers, oligosaccharides, polysaccharides, nucleotides, oligonucleotides and nucleic acids, including DNA and RNA, protein nucleic acid hybrids, small molecules and physiologically active analogues thereof. Further, the modifiers may be derived from natural sources or made by recombinant or synthetic means and include analogues, agonists and homologs.

Pharmaceuticals may be substances which are prophylactically active. In particular, such substances include immunogens such as vaccines. Suitable vaccines include, but are not limited to, live and attenuated viruses, nucleotide vectors encoding antigens, live and attenuated bacteria, antigens, antigens plus adjuvants and haptens coupled to carriers. Particularly preferred are vaccines effective against diphtheria, tetanus, pertussis, botulinum, cholera, Dengue, Hepatitis A, B, C and E, *Haemophilus influenza* b, herpes virus, *Helicobacterium pylori*, influenza, Japanese encephalitis, meningococci A, B and C, measles, mumps, papilloma virus, pneumococci, polo, rubella, rotavirus, respiratory syncytial virus, Shigella, tuberculosis, yellow fever and combinations thereof. The antigenic component of vaccines may also be produced by molecular biology techniques to produce recombinant peptides or fusion proteins containing one or more portions of a protein derived from a pathogen. For instance, fusion proteins containing an antigen and the B subunit of cholera toxin have been shown to induce an immune response to the antigen. Sanchez at al. (1989) *Proc. Natl A cad Sci. USA* 86:481-0.485. Vaccines are particularly suitable for incorporation into the single-dosage composition. They are stable indefinitely under ambient conditions and can be redissolved in sterile diluent immediately before inoculation. Preferably, the immunogenic composition contains an amount of an adjuvant sufficient to enhance the immune response to the immunogen. Suitable adjuvants include, but are not limited to, aluminium salts, calcium phosphate, squalene mixtures (SAF-1), muramyl peptide, saponin derivatives, mycobacterium cell wall preparations, monophosphoryllipid A, mycolic acid derivatives, non-ionic block copolymer surfactants, Quil A, cholera toxin B subunit, polyphosphazene and derivatives, and immunostimulating complexes (ISCOMs) such as those described by Takahashi at al. (1990) *Nature* 344:873-875. For veterinary use and for production of antibodies in animals, antigenic components of Freund's adjuvant can be used. As with all immunogenic compositions, the immunologically effective amounts of the immunogens must be determined empirically. Factors to be considered include the immunogenicity, whether or not the immunogen will be complexed with or covalently attached to an adjuvant or carrier protein or other carrier, route of administration and the number of immunising dosages to be administered. Such factors are known in the vaccine art and it is well within the skill of immunologists to make such determinations without undue experimentation. Multiple pharmaceuticals can be included in the syringe or insert of the present invention. Thus, the syringe or insert may contain two or more different vaccines, for example 2, 3, 4 or 5 different vaccines.

The compressible porous matrix insert of the invention is a body of compressible porous matrix having in it a glass which contains a pharmaceutical, which is suitable for insertion into the barrel of a syringe. The syringe of the present invention has such a compressible porous matrix pre-inserted in its barrel. The compressible porous matrix may be in the form of a block, a cylinder, or a prism, optionally an elongate block, cylinder or prism, which may have a circular or a non-circular (e.g. rectangular) cross section.

The compressible porous matrix may comprise a coloured substance. The coloured substance may be an inert, non-toxic, injectable substance which is present on the matrix in addition to the pharmaceutical. Alternatively the pharmaceutical itself may be a coloured substance. The coloured substance may be present on the external surfaces of the matrix, or additionally or alternatively on the internal surfaces of the matrix. The coloured substance gives a colour to the matrix when the syringe barrel contains a carrier liquid, which colour is reduced following depression of the plunger in the syringe barrel to discharge the carrier liquid from the syringe. During use of the syringe, when the carrier liquid comprising the pharmaceutical is forced out of the outlet at the needle end of the syringe barrel, at least some of the coloured substance flows away from the matrix, thereby reducing the colour of the matrix. The reduction in colour of the matrix is thus associated with successful delivery of the pharmaceutical. The user of a syringe containing the matrix is able to determine whether the pharmaceutical has been delivered to the subject.

The present invention also provides methods for producing the syringes and inserts of the invention, as well as methods of using and uses of the syringes and inserts in the delivery of a pharmaceutical to a subject.

The present invention provides a method of producing a pharmaceutical syringe or a compressible porous matrix insert. The method comprises contacting a compressible porous matrix with a solution of a glass-forming material containing a pharmaceutical. The solution of glass-forming material containing the pharmaceutical may enter the cells of the matrix by capillary action, and thereby coat the internal surfaces of the matrix (the surfaces formed by the cells). Contacting the matrix with the glass-forming solution may comprise dipping the matrix partially or completely into the solution, or spraying the matrix with the glass-forming solution. The matrix is then dried, preferably air dried, such that the glass-forming solution in the matrix dries to form a glass which comprises the pharmaceutical. The method may further comprise treating the matrix with a blocking agent before contacting it with the glass forming solution. Alternatively or additionally, the method may further comprise treating the matrix with a surfactant.

The present invention also provides a method of pre-loading a syringe with a pharmaceutical, comprising inserting the compressible porous matrix insert of the invention into the barrel of a syringe. Any conventional syringe may be used, and thereby pre-loaded with pharmaceutical. The amount of pharmaceutical present in the glass on the compressible porous matrix insert may correspond to a fixed or predetermined dose of that pharmaceutical.

The invention also provides a method of preparing a pharmaceutical for administration or delivery (e.g. injection) to a subject. In this method the compressible porous matrix insert of the invention is inserted into the barrel of a syringe, as described above, and then a carrier liquid is forced through the compressible porous matrix so that the pharmaceutical becomes dissolved or dispersed in the carrier liquid prior to delivery to the patient. In this method, after insertion of the insert into the barrel of the syringe, a carrier liquid (e.g. water, saline) is drawn into the syringe. The carrier liquid may then enter the matrix by capillary action, causing the glass on the matrix to dissolve. The pharmaceutical thus becomes dissolved, suspended, or dispersed in the carrier liquid. When the carrier liquid is then forced out of the syringe by depressing the plunger the matrix is compressed, thereby forcing the carrier liquid out of the matrix, such that the pharmaceutical in which it is dissolved or suspended is forced out of the syringe.

The invention also provides a method of using a syringe or insert of the invention for delivering or administering a pharmaceutical to a subject (i.e. a patient). The method may comprise the method of preparing a pharmaceutical for administration or delivery to a subject as described above, and then delivering the pharmaceutical to the patient by the normal injection process of depressing the plunger of the syringe which compresses the porous matrix to expel the pharmaceutical into the injected liquid and thereby into the patient.

The invention also provides a kit of parts, comprising a compressible porous matrix insert of the invention, a syringe barrel, and a syringe plunger. The insert is suitable for inserting into the syringe barrel. The kit may further comprise a carrier liquid, which carrier liquid is an aqueous solvent or an organic solvent. In use the carrier liquid acts as a solvent for dissolving the glass, such that the pharmaceutical in the glass becomes dissolved, suspended or dispersed in the carrier liquid. The kit may further comprise a needle for connecting to the needle end of the syringe barrel.

The carrier liquid is a liquid for carrying the pharmaceutical for delivery to a subject. The carrier liquid acts is a solvent for the glass in which the pharmaceutical is contained. The carrier liquid may be an aqueous solvent (an aqueous liquid) or an organic solvent (an organic liquid). Preferred carrier liquids are water (specifically sterile water for injection, or bacteriostatic water for injection) and saline (specifically physiological saline).

The present invention also provides a pharmaceutical syringe or compressible porous matrix insert as described herein, wherein the insert is fixed to the seal of a syringe plunger. The insert may be fixed to the seal by any means, for example by a glue or a fastening. The syringe plunger bearing the insert is suitable for use with a syringe barrel to provide an operable syringe.

An example of the invention, and experimental results underlying the present invention, will now be described by referring to the accompanying drawings:

FIG. 1 Shows the improved syringe as supplied with the dry pharmaceutical in a porous matrix in the barrel FIG. 2 is a transverse cross section showing the rehydrated porous matrix and its relationship with the walls of the barrel FIG. 3 shows the filling of the syringe with sterile water or saline and rehydration of the vaccine for injection FIG. 4 shows the injection of the solubilised pharmaceutical and it's expulsion from the porous matrix by compression FIG. 5 shows the results of experimental example 3.

DETAILED DESCRIPTION OF THE FIGURES

Figure 1A:
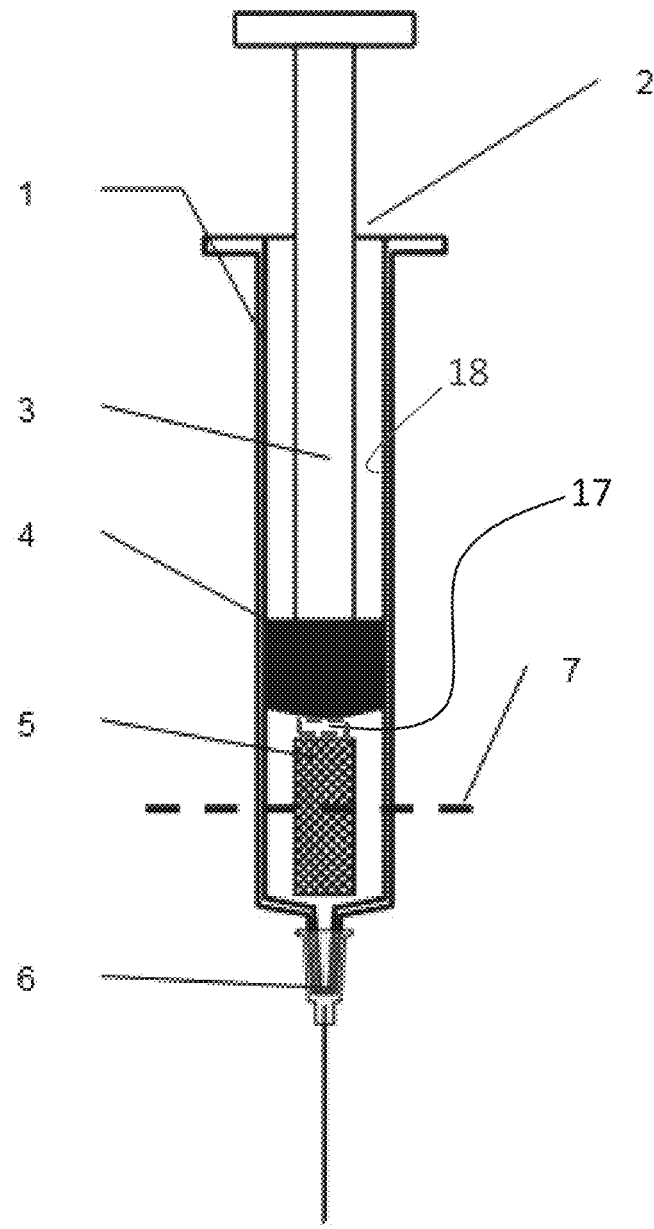
Figure 1B:
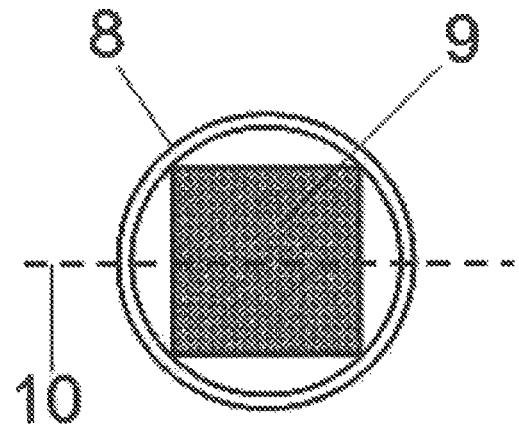

FIG. 1a: Axial cross-section through a syringe containing the pre-loaded porous matrix. The syringe is illustrated in the configuration as it is in storage. The syringe barrel 1 has an open end 2 through which is inserted a plunger 3 with an attached sealing member 4 making a water-tight seal with the interior syringe barrel wall 18 of the barrel which houses the dried porous matrix 5 containing the glass-stabilised product. In certain embodiments, the porous matrix 5 may be fixed to the seal by, for example, a glue or a fastening 17. The porous matrix is located inside the barrel between the sealing member and the needle end with its attached hypodermic needle 6. The dashed line 7 is the location of the transverse cross section in FIG. 1b FIG. 1b: Transverse cross section of one configuration of the porous matrix, after it has been rehydrated to its original dimensions, showing the circular barrel of the syringe 8 containing a porous sponge of rectangular cross section 9 which makes contact with the barrel inner surface only at the corners leaving a circle-segment shaped space on each of the sides which allows the free passage of any trapped air during purging of the syringe. The axial cross sections of FIGS. 1a, 2, 3 and 4 are made at the location of the dashed line 10.

Figure 2:
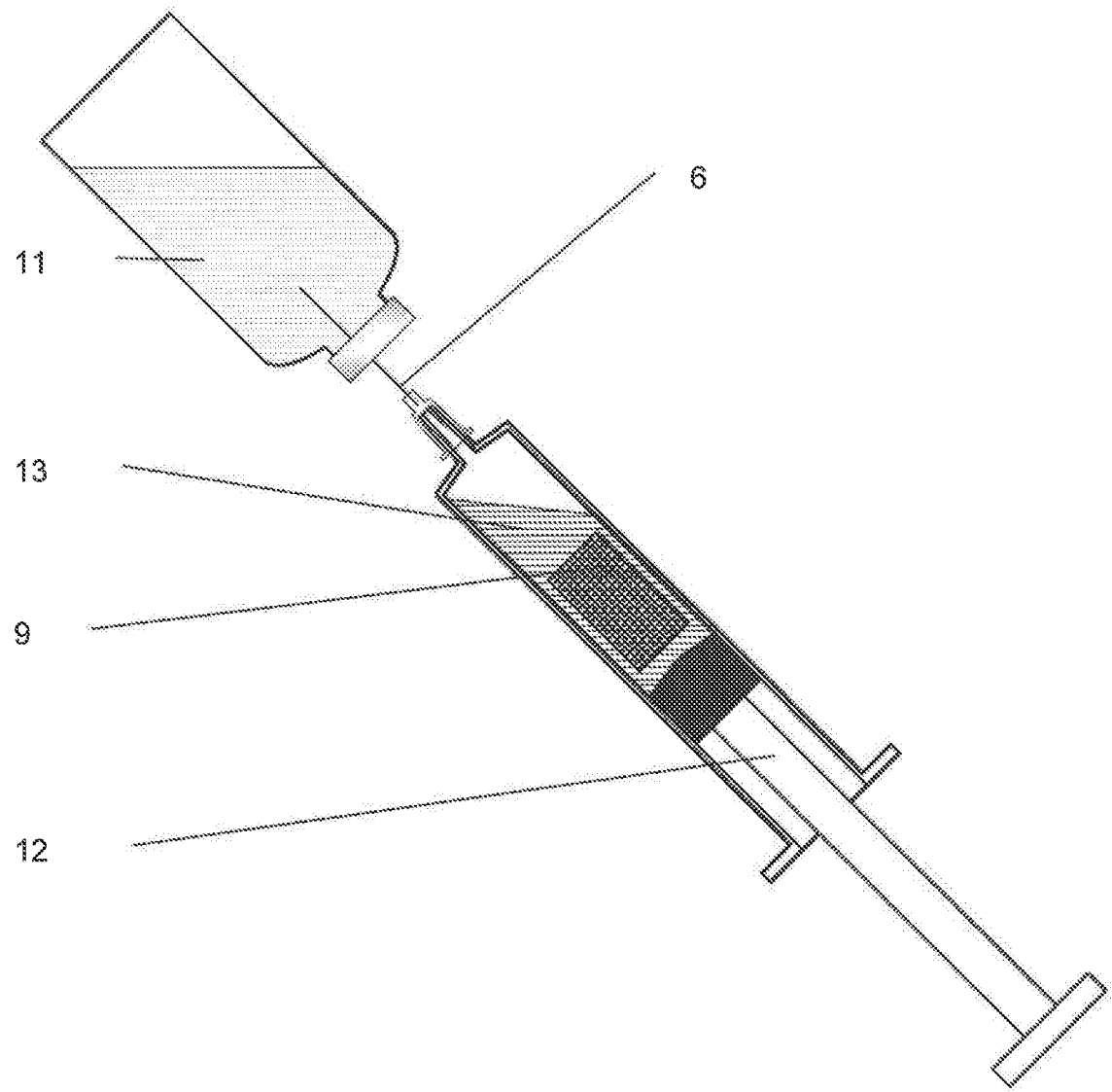

FIG. 2: Axial cross-section through a syringe containing the porous matrix 9 rehydrated after the needle 6 is inserted into a vial of sterile water for injection 11, by withdrawal of the plunger 12 which rehydrates the porous matrix 9 with the aspirated water 13 and dissolves the glass stabilised vaccine.

Figure 3:
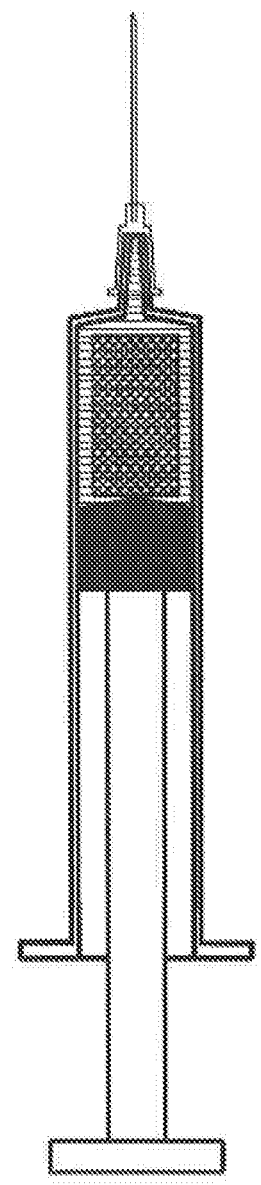

FIG. 3: Axial cross-section through a syringe containing the porous matrix in the inverted position, after the air has been expelled through the needle, ready for injection.

Figure 4:
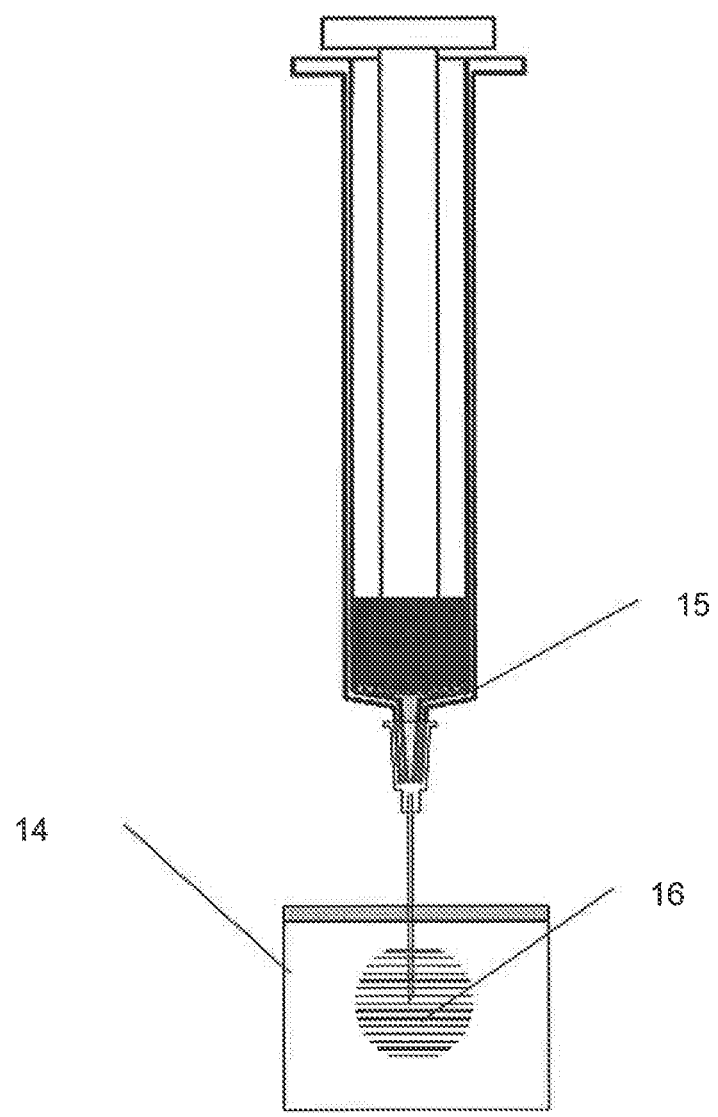

FIG. 4: Axial cross-section through a syringe containing the porous matrix at the point of injection when the needle is inserted into the subcutaneous, intramuscular or intravenous location 14. By depressing the plunger completely to the needle end, the porous matrix is compressed 15 to expel the full dose into the injection site 16.

Figure 5:
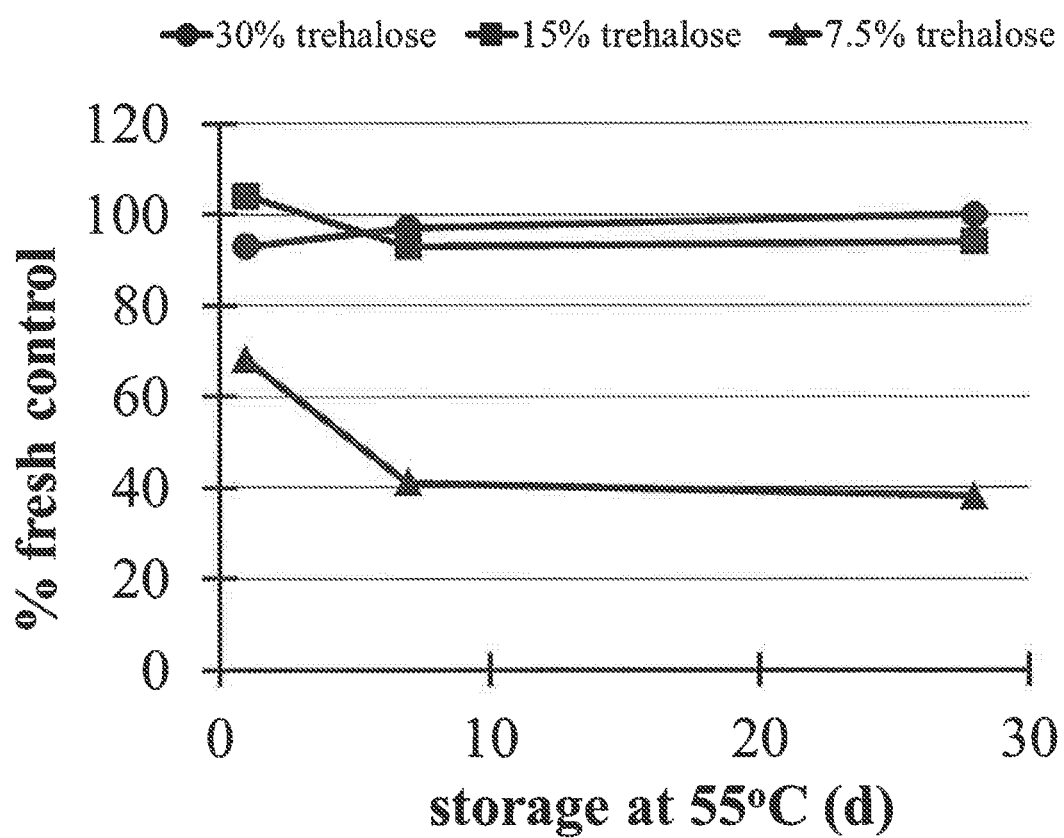

FIG. 5: Aluminium hydroxide was dried in 7.5% w/v, 15% w/v and 30% w/v trehalose buffer and recovered up to 30 days after storage at 55° C. Recovery was measured by column sedimentation. At 15% w/v trehalose concentration and above this adjuvant is recovered fully intact.

Figure 6A:
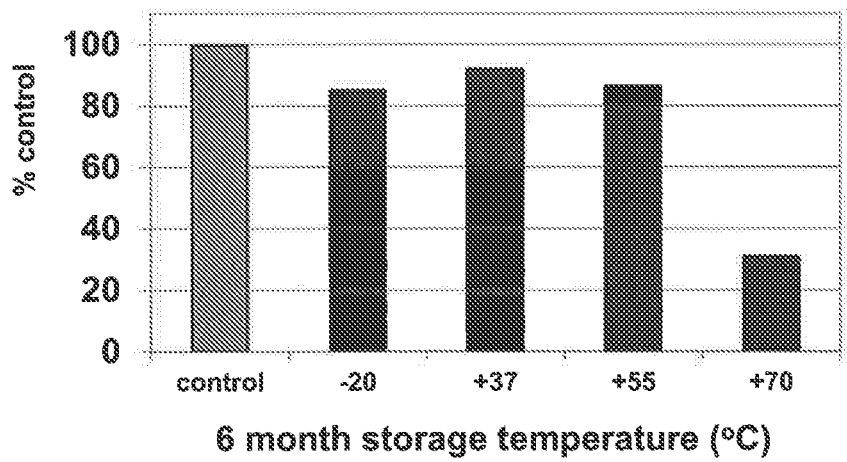
FIGS. 6A and 6B show the results of experimental example 5.

FIG. 6A: Recovered dried HepB shows long term stability after storage at various temperatures for six months. The majority of the vaccine is recovered in intact form except at 70° C. Control is fresh (non-stored) vaccine.

Figure 6B:
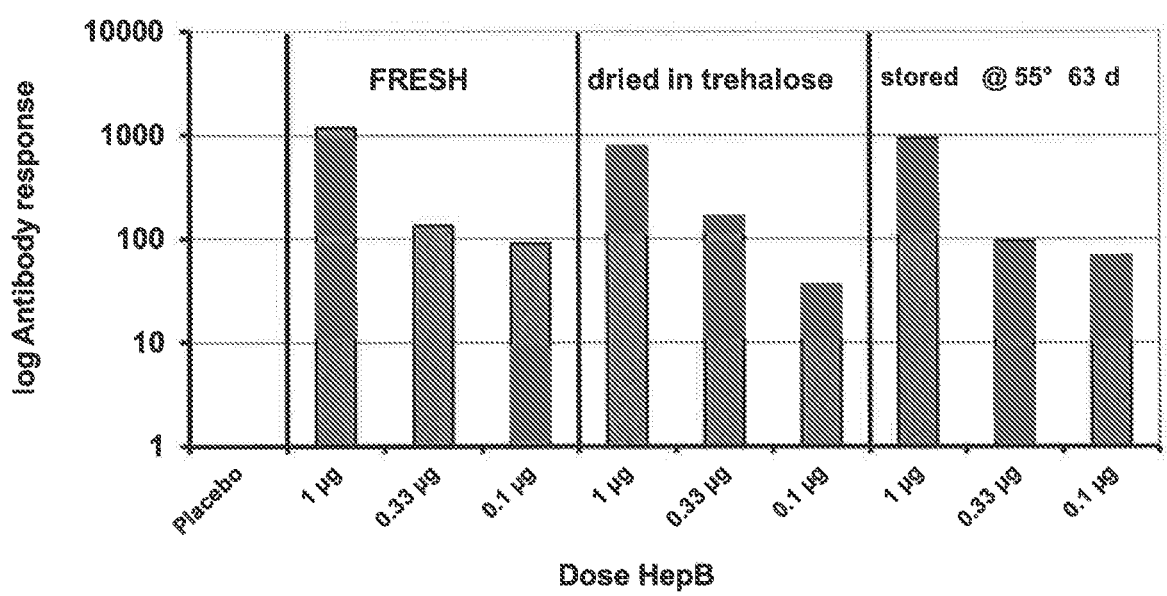

FIG. 6B: Antibody response of groups of 5 mice given three different doses of Hepatitis B vaccine either fresh or stabilised in trehalose with storage at 55° C. for two months. All responses are equivalent to fresh vaccine within the variability of the assay.

Figure 7A:
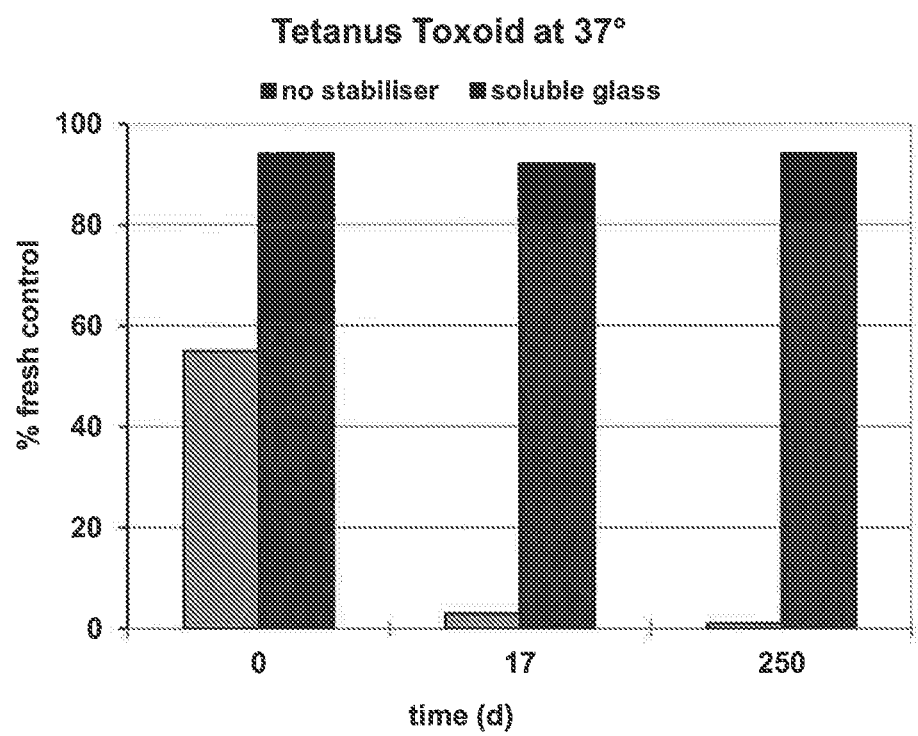
FIGS. 7A and 7B show the results of experimental example 6.

FIG. 7A: Recovery of adjuvanted tetanus vaccine after drying in trehalose buffer and storage for more than eight months. While non-stabilised vaccine lost some activity on drying and all activity on storage, stabilised vaccine was recovered intact. Recovery of intact vaccine was determined by immunoassay.

FIG. 7B: Antibody levels measured in three groups of 10 mice at 4, 8 or 12 weeks after injection with either fresh (non-stored) vaccine or two different dried formulations of trehalose buffer (treh 1 and treh 2) stored at 37° prior to injection The immune response of the mice to both dried preparations was equivalent to fresh vaccine within the variability of the assay.

Obviously, variations can be made to the described format without departing from the substance of the invention. For example, the product could be a vaccine drug or any biological material that would normally be subject to degradation if stored in liquid solution or suspension. This includes products such as hormones, protein and viral vaccines and genetic material. The glass forming material could be any non reactive glass-forming sugars such as trehalose, raffinose or sucrose or mixtures of sugars or any other carbohydrate glass-former; also glass-forming amino acids such as monosodium glutamate (MSG), monosodium aspartate (MSA) or a MSG/MSA mixture or other soluble stabilising glasses or mixtures of the above could be used; and the syringe could be either a standard syringe or an auto-disable syringe or other liquid delivery device or a device for mass inoculations. In an alternative embodiment, the carrier liquid could be an emulsion of the oil-in-water or water-in-oii type and as such the active product could become associated with the aqueous phase of the emulsion as the aqueous phase dissolves the glass. In a further alternative, an oil solvent could be used in conjunction with a hydrophobic pharmaceutical stabilised in an oil soluble glass.

DETAILED DESCRIPTION

The present invention is an improvement on the syringes typically used to give parenteral injections of pharmaceutical agents. It incorporates the pharmaceutical material stabilised by drying it in a solution of a stabilising excipient, for example trehalose, to form a glass in a three dimensional and compressible porous matrix which is then located within the barrel of a conventional plastic syringe between the plunger and the needle fitting. This syringe can then be stored for prolonged periods at ambient temperatures and is ready for instant use. Upon drawing up the water for injection, capillary action draws the solvent liquid into the porous matrix and the soluble glass therein rapidly dissolves to release the pharmaceutical into the liquid for injection. A significant advantage of the present invention is that it uses no additional housings and is designed to be made with minimal change to existing manufacturing processes. In use it also requires no changes from standard injection technique and requires no training. It is therefore of minimal cost.

In a preferred realisation of the present invention the pharmaceutical material is dried in a compressible porous matrix in a wide range of possible sizes and is then introduced into the barrel of an appropriately sized syringe, which syringe typically has an internal volume larger than the matrix. Thus even a large volume of porous matrix can be accommodated in the syringe and a consequently large volume of active product dried therein.

For example a compressible porous matrix in the form of a rectangular block measuring 6 mm×6 mm×10 mm in its non-compressed state, and having a glass comprising a pharmaceutical in it, may be introduced into the barrel of a 2 ml syringe (a syringe having a maximum dispensing volume of 2 ml). In this example the compressible porous matrix in its non-compressed state occupies 18% of the volume of the syringe barrel (the nominal internal volume of the syringe). The compressible porous matrix in its non-compressed state may occupy at least about 10%, at least about 20%, at least about 30%, at least about 40%, at least about 50%, at least about 60%, at least about 70%, at least about 80%, at least about 90%, about 10-90%, about 20-90%, about 30-90%, about 40-90%, about 50-90%, about 10%, about 20%, about 30%, about 40%, about 50%, about 60%, about 70%, about 80% or about 90% of the volume of the syringe barrel into which it is to be inserted for use. Typical syringes for use in the present invention will have volumes of between about 1-10 ml, and therefore typical compressible porous matrix blocks for use in the present invention may have volumes of between about 0.1-9 ml (100-9000 $mm^3$) depending on which size of syringe they are to be inserted into for use. The volume of a syringe refers to the volume of the barrel of the syringe, that is the internal volume of the cylindrical compartment in the syringe which holds the liquid for injection (so, for example, a "2 ml syringe" has a barrel volume of 2 ml), The compressible porous matrix may be biased towards its non-compressed (expanded) state, which means that during use depression of the syringe plunger is needed in order to force the porous matrix into its compressed form.

In addition to the standard disposable plastic syringes a variety of other injectors maybe used. These include without restriction, glass syringes, auto-disable syringes, retractable needle syringes and other injection devices. Such devices may have a compartment for holding a liquid for injection comprising a compressible porous matrix insert of the invention. The compressible porous matrix of the invention may be suitable for inserting into the liquid-holding compartment of such a device. Thus the present invention provides a method of storing and or transporting a pharmaceutical stabilized in a glass that is soluble in a carrier liquid, wherein the pharmaceutical is stored in a compressible porous supporting structure in a passage for the flow of the said liquid so that the agent can be administered by aspirating the carrier liquid into the spaces or pores of the supporting structure and then causing the liquid to be expelled through the passage and thence to the patient as the porous supporting structure is compressed.

Many drugs and highly multivalent vaccines can easily be stabilised in the syringe with a minimal requirement for prior concentration. A normal injection procedure is used in which the practitioner inserts the needle into a vial of sterile water or saline and withdraws the required volume of liquid into the syringe and then injects the active product into the patient. This is the procedure currently used and is familiar to health care workers, thereby reducing the need for additional training and the chances of error. Indeed, because the appropriate dose is already in the syringe as supplied, any error in the volume of liquid aspirated (providing it is sufficient to dissolve the pharmaceutical) does not alter the dose delivered to the patient In another novel realisation of the present invention the porous matrix containing the pharmaceutical product is easily compressed after rehydration. The aspiration of the water starts the dissolution of soluble glass containing the pharmaceutical as the liquid permeates the porous matrix by capillarity. For injection, the plunger of the syringe is depressed, preferably fully depressed, causing the compression of the porous matrix thus expelling the liquid contained therein, preferably all, or essentially all of the liquid contained therein, and the full dose of the pharmaceutical is delivered into the patient. The injection process can also be made to activate the disabling step of an auto-disable syringe rendering it incapable of reuse.

A compressible porous matrix comprising a pharmaceutical is a compressible porous matrix insert, suitable for inserting into the barrel of a syringe for use in delivery of the pharmaceutical. In use, the compressible porous matrix is compressed by the action of depressing the syringe plunger, that is, the action of urging the syringe plunger towards the needle end of the syringe barrel. In use, the syringe plunger draws a volume of solvent, or carrier liquid, (e.g. sterile water, saline) into the barrel of the syringe by the action of raising the plunger, that is the action of urging the syringe plunger towards the open end of the syringe barrel (away from the needle end of the syringe barrel). The solvent rehydrates the porous matrix. The solvent is drawn into the porous matrix and dissolves the glass in which the pharmaceutical is comprised, such that the pharmaceutical becomes dissolved or suspended in the carrier liquid. The plunger is then depressed to deliver the pharmaceutical to a subject. This depression of the plunger compresses the porous matrix into its compressed state.

The compressibility of the porous matrix is advantageous because the action of compressing the porous matrix forces pharmaceutical out of the porous matrix, where it would otherwise tend to be held in the carrier liquid by the capillarity of the porous matrix. The action of compressing the porous matrix forces the pharmaceutical out of the syringe for delivery to a subject. Preferably in use the action of depressing the syringe plunger is capable of forcing out of the syringe (i.e. discharging or expelling from the syringe barrel) at least about 60%, at least about 70%, at least about 80%, at least about 90%, at least about 95%, at least about 98%, at least about 99% or substantially 100% of the pharmaceutical, that is the pharmaceutical that was in the glass.

We have found that some porous matrices although hydrophilic, absorb water slowly. This problem can be overcome and water uptake greatly accelerated by the addition of small quantities of an inert biocompatible surfactant to the glass-forming solution prior to loading the matrix with the pharmaceutical in the stabilising solution and drying. When such a syringe eventually comes to be used, the surfactant dried in the matrix facilitates the uptake of solvent and the rapid rehydration of the glassified product. The use of surfactant in the same way can even render certain hydrophobic foams suitable as matrices for water-soluble products. Examples of suitable surfactants include without limitation polyoxyl castor oils, polysorbates and other injectable surfactants approved by regulatory authorities.

In some cases however, the recovery of the product may be reduced by physicochemical binding of the substance to the surfaces of the porous matrix. This can be overcome by prior treatment of the porous matrix with a blocking agent optionally followed by washing to remove surplus blocking agent and re-drying. Examples of blocking agents include, without limitation, proteins like caseins or serum albumins, surfactants such as the polysorbate detergents Tween 20 or Tween 80 or polymers such as polyvinyl pyrrolidone or polyvinyl alcohols.

In manufacture of the present invention, the pharmaceutical product is mixed, either dissolved or in suspension, with preservative solution. It is absorbed by capillarity into the porous matrix and then dried by any simple process such as air drying, vacuum drying, freeze drying etc. Preferably it is dried outside the syringe. Preferably, the preservative solution (glass-farming solution) is dried by air drying to form a glass (i.e. a noncrystalline solid). Air drying is convenient, inexpensive, and may be done at any ambient temperature (e.g. room temperature), at about 15° C. or higher, about 20° C. or higher, about 25° C. or higher, about 30° C. or higher, at about 40° C. or higher, at about 50° C. or higher, at about 60° C. or higher, at about 70° C. or higher, at about 10° C. to about 70° C., at about 10° C. to about 60° C., at about 10° C. to about 50° C., at about 20° C. to about 70° C., at about 20° C. to about 60° C., at about 20° C. to about 50° C., at about 20° C. to about 40° C., at about 15° C. to about 45° C., at about 20° C. to about 40° C. or at about 18° C. to 25° C. Air drying may be done at atmospheric pressure (approximately 100 kPa). The preservative solution may be dried by air drying overnight, or over a period of about 1, 2, 4, 8, 16 or 24 hours or more. A low relative humidity may be used during drying, for example of between about 0-20% or 2-10%. Glass formation may optionally be facilitated by using a solution purged of any less soluble solids by filtration and/or by boiling. Drying a preservative solution on a porous matrix outside the syringe is convenient and low cost, compared with methods of drying a preservative solution while it is inside the barrel of the syringe. This is at least partly because drying a preservative solution on a porous matrix outside the barrel of the syringe may be done by air drying, rather than vacuum drying or freeze drying.

In the present invention a pharmaceutical is included in the glass-forming solution before drying and is stabilised in the resultant glass. Methods for stabilising products such as pharmaceuticals (including biological therapeutics) are known and are described for example in U.S. Pat. No. 4,892,319, GB2187191, U.S. Pat. No. 5,955,448, WO96/40077 and WO2011/098837. In the present invention, the glass containing the stabilised pharmaceutical may form a layer on the surfaces of the voids or cells in the compressible porous matrix. The relative thinness of this layer means that the pharmaceutical-containing glass dries very rapidly and thoroughly and then subsequently dissolves relatively quickly upon contact with a solvent that may be drawn into the barrel of a syringe for injection (e.g. sterile water or saline).

Examples of preservatives include, without limitation, trehalose, raffinose or sucrose and structural isomers thereof or mixtures of these or any other carbohydrate glass former, glass-forming amino acids such as monosodium glutamate (MSG), monosodium aspartate (MSA) or a MSG/MSA mixture or other soluble stabilising glasses may also be used. The manufacturing process requires minimal additional equipment to that currently used. Because the volume of each of the porous matrices used with any particular product at the same they can be loaded with the correct dose of product by precise delivery to each dry matrix insert when the dose is uniformly distributed by capillary action.

Alternatively because the capillarity of each porous matrix insert precisely made from the same batch is essentially the same, each insert will naturally aspirate the same volume of drug from bulk solution. For pharmaceuticals where the dose is not excessively critical, this can provide a simple and inexpensive method for dosing the syringes with standard doses of pharmaceutical. The improvement is made by simply inserting the dried porous matrix into a standard syringe, such as a disposable plastic one, so that costs are little affected, making these improved stable products competitively priced with existing ones.

The nature of the porous matrix insert used in the syringe is not restricted and alternatives maybe obvious to those skilled in the art. A porous, open-cell foam or sponge has been found to be ideal but flexible woven or felted fabric on which the active product is glass-dried and which is then folded or crumpled into the syringe barrel can also work, in fact, any compressible porous matrix whether made by foaming or by woven or felted fibres is suitable. The porous matrix should be of high grade, sterilisable, suitable for housing parenterally injectable substances and that it is not particle or fibre-shedding nor contains toxic extractable chemicals. The porous matrix should be insoluble. The matrix, which is compressed against the aperture to the needle by the plunger, should not obstruct the aperture. In practice, appropriate matrices with good open cell structure are still fully porous when compressed and do not suffer from this problem. For the usual water soluble pharmaceuticals a preferred feature is that the porous matrix be of a hydrophilic nature in order to readily absorb the solution of pharmaceutical by capillarity and to redissolve it for injection. Example materials in the manufacture of the porous matrix include, without limitation, open cell foamed materials such as cellulose or melamine foams; felted material such as polyester fibre locked needlefelt or woven fabrics such as silk, cotton or synthetic hydrophilic fabrics that are sufficiently soft to be folded, crumpled or compressed for insertion into the syringe barrel. Preferred matrices are cellulose foam, polyurethane foam and melamine foam.

In a preferred embodiment of the invention, simple refinements of the porous matrix render the syringe easier to use. After the aspiration of the water there remains a volume of air in the syringe that was present before aspiration and it must be removed by venting before injection. It is also important to avoid forcing the air through the porous matrix insert thereby displacing the liquid when venting the air before injection. To preserve the simplicity and familiarity of use, the air should be vented by the usual manoeuvre, of expelling the air by holding the syringe vertically with needle uppermost and driving the air out through the needle by depressing the plunger until the syringe contains liquid only. Preferably, therefore, the compressible porous matrix is shaped and/or sized to provide a gap for passage of air through or around the matrix when the matrix is inserted in the syringe barrel, for allowing passage of air through the gap on venting of the syringe.

The syringe of the invention may have a gap for the passage of air during venting of the syringe, which gap is present between the matrix and the inner wall of the syringe barrel. When the syringe contains a carrier liquid and the needle end of the syringe is held uppermost, the gap allows air bubbles to move to the outlet at the needle end of the syringe and to be expelled from the syringe before injection. Such a gap can be provided in a syringe barrel of circular cross section by providing a compressible porous insert which is a block, cylinder or prism having a non-circular cross section, for example a cuboidal or rectangular block or a cylinder having an oval cross section. Venting of the syringe can also be facilitated by various modifications including making the porous matrix insert non-circular, for example square, in cross section and located inside the circular barrel without lateral compression. For example, when the porous matrix insert is square in cross section any air trapped between the porous matrix insert and the plunger is easily vented around the insert via the circle-segment shaped gaps between the flat sides of the insert and the circular inner surface of the barrel. Capillary forces in the matrix ensure the liquid remains in the insert during this venting. A similar refinement can also be achieved by fabricating the porous matrix as a cylindrical shape with an external diameter smaller than the internal diameter of the barrel or as a hollow cylinder fitting snugly in the barrel. Other formats of the porous matrix to achieve easy air venting are obviously possible and are evident to the skilled practitioner. In a further realisation the porous matrix insert containing the stabilised pharmaceutical material is fixed to the seal at the end of the syringe plunger so that entrained air is naturally located above the insert during the venting manoeuvre. The porous matrix insert may be fixed to the seal by, for example, a glue or a fastening. The geometry of the insert may then vary from a centrally located cylinder, a cylinder that occupies the full diameter of the syringe barrel, or alternative shapes and sizes that facilitate rapid release of the contained stabilised pharmaceutical. The cross-sectional diameter, or cross-sectional maximum width (width at the widest point of the transverse cross section; transverse to the longitudinal axis of the syringe when inserted), of the porous matrix insert may be smaller, around the same as, or larger than the internal diameter of the syringe barrel. If the cross-sectional diameter, or maximum width, of the porous matrix insert is larger than the internal diameter of the syringe barrel, then the insert may be inserted into the barrel with lateral compression. A further refinement can be the addition of an inert, non toxic, injectable, coloured substance to the active product, thus altering the observed colour of the porous matrix insert when it is absorbed and dried. The colour can be made specific to the particular pharmaceutical thus identifying which product is present in the syringe and ensuring the injection of the correct one. After use, the colour flushes from the porous matrix along with the active product thus uncovering the native colour of the matrix. Completeness of colour change can demonstrate injection of the full dose of active product. Also, the loss of colour in the porous matrix shows that the syringe has been used and reduces the possibility of accidental reuse. Suitable coloured substances include fluorescein.

Of course the quantity of pharmaceutical material stored and delivered in this method described herein can vary over a very wide range by tailoring the size of the porous matrix insert to fit any size of syringe. Since the porous matrix is chosen to have a very high capacity to absorb water (of the order of 50 millilitres per gram), there is needed little or no additional increase in the size or the bulkiness of the syringe to accommodate the porous matrix insert. Theoretically, there is no physical limit to the size of the syringe or the contained insert.

The present invention is further illustrated by the following 7 Examples that are illustrative and are not intended to be limiting in their scope.

EXAMPLES

In these studies of the glass-forming solutions used contained dissolved trehalose at a concentration of 10-20% My or 10-30% w/v. The solutions were either dried by air drying at about 50° C., or spray drying at about 45° C.

Example 1

Materials Suitable as the Porous Matrix

A programme of selection for the properties of the optimal porous matrix screened 36 foams, sponges and fibrous felts some of which were rejected because they were non absorbent closed-cell foams or of inappropriate pore sizes. Analysis of the remaining open cell matrices identified as foamed materials possessing most of the properties required, cellulose foam, melamine foam and hydrophilic reticulated polyether foam. A comparison of these showed that cellulose foam (FT-SPX Foam Techniques, Northants, NN8 6GR, UK) was superior to the others in that it was very absorbent, easy to wash clean and sterilise, free of plasticisers and other toxic additives, dried rapidly and evenly and was inexpensive. Commercial Melamine foam (FT-11 M Basotect, density 11 kg/m$^3$, Foam Techniques, Northants, NN8 6GR, UK) also hydrated instantly on re-wetting without entrapped air bubbles and was soft and very compressible on injection releasing nearly all of the absorbed liquid.

Example 2

Testing Release of Model Product

A model system was used to examine the behaviour of a porous matrix in the syringe. Rectangular blocks of cellulose foam measuring 6 mm×6 mm×10 mm were saturated with 10% w/v sugar glass forming solution containing a red Carmoisine dye and placed in an oven at 40° C. It was fully dried within 2 hours with slight but obvious shrinkage. It was loaded into a 2 ml plastic syringe. 0.8 ml of water was then aspirated into the syringe. The dry porous matrix immediately filled with water by capillary action, regained its previous volume when wet and the dye began to dissolve into the water. The air bubble was readily expelled from the syringe in the usual way. The liquid was then injected dropwise into a glass vessel by depressing the plunger to fully compress the porous matrix insert. All or nearly all of the dye appeared in the receiving vessel. On withdrawing the plunger after injection the porous matrix insert partially re-expanded to reveal that the Carmoisine had been expelled so that the porous matrix had nearly reverted to its native colour with only a pale residual pink colour.

Example 3

Recovery of Particulate Aluminium Hydroxide Adjuvant

The possible entrapment of colloidal particles or aggregates within the pores of the matrix was tested by using the approved vaccine adjuvant Aluminium hydroxide. Recovery of this material is essential for the use of vaccines in the syringe since a major proportion of the vaccine antigens are physicochemically bound to the adjuvant and would be lost if significant entrapment occurred. This colloidal substance in aqueous suspension was mixed with trehalose solution and dried Measurement of the quantity of adjuvant loaded and the amount recovered indicated recovery of about 90% of the adjuvant. The results of this experiment are shown in FIG. 5. In embodiments of the invention, the colloidal substance in aqueous suspension may be mixed with trehalose and dried in a porous cellulose porous matrix block. The block could be inserted into the barrel of a 2 ml syringe and 0.6 ml of water aspirated to measure the recovery of aluminium hydroxide adjuvant. Air may be expelled and the contents of the syringe injected into a vial. Based on the results shown in FIG. 5, measurement of the quantity of adjuvant loaded into the porous matrix would be expected to indicate recovery of about 90% of the adjuvant.

Example 4

Recovery of Model Protein Pharmaceutical

Alkaline phosphatase enzyme was used as a model protein for stability and recovery studies. It was loaded and dried in a porous matrix. Some matrices were placed into stability studies. The recovery of protein from the matrix was then measured. Substantially all the protein as measured by enzymatic activity was recovered even after storage at 37° C. or 45° C. for three months. Variation of the numerical result is the result of variability in the assay. These results indicate approximately 100% recovery of active protein. The results of this experiment are shown in Table 1, below. In embodiments of the invention a protein of interest may be loaded and dried in a porous matrix block (e.g. a cellulose porous matrix block). The block could then be placed in a syringe. Some syringes could then be placed in stability studies to measure recovery of protein from the matrix. Based on the results shown in Table 1, below, substantially all the protein as measured by enzymatic activity would be expected to be recovered after storage at 45° C. for three months.

TABLE 1

| | % Alkaline phosphatase recovered | |
| --- | --- | --- |
| Experiment | Matrix stored at 37° C. | Matrix stored at 45° C. |
| 1 | 100.4 | 111.3 |
| 2 | 85.5 | 92.7 |
| 3 | 99.8 | 82.4 |

Example 5

Recovery of Adjuvanted Hepatitis B Vaccine

The adjuvanted vaccine Hepatitis B was dried in a trehalose buffer. Some were set up for stability studies (results shown in FIG. 6A), others used for recovery experiments and a third set were put into stability studies and after a period were tested for their immunogenicity in mice (results shown in FIG. 6B), The results showed that immediate recovery, recovery after stability studies and immunogenicity of this vaccine were all equivalent to fresh vaccine.

Example 6

Recovery of Adjuvanted Tetanus Toxoid Vaccine

Figure 7B:
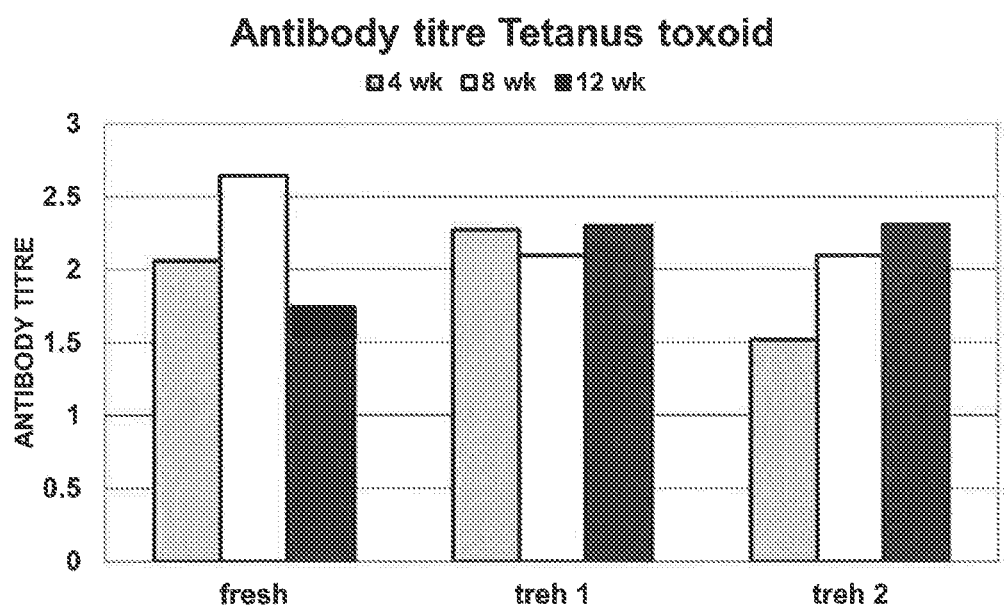

To confirm the generality of the findings adjuvanted tetanus toxoid vaccine was dried as above on a porous matrix. Some were set up for stability studies, others used for recovery experiments (results shown in FIG. 7A) and a third set were put into stability study conditions and after a period were tested for their immunogenicity in mice by measuring serum antibodies (results shown in FIG. 7B). The results showed that immediate recovery and, recovery after stability studies and immunogenicity of this vaccine were all equivalent to fresh vaccine.

Example 7

Potency of Recovered Stabilised Vaccine

To ensure that the protective clinical effect of vaccination is retained when using this technology, syringes loaded with stabilised tetanus vaccine as in example 6 are used to vaccinate mice which are then challenged with a lethal dose of active tetanus toxin. It is shown that the stabilised vaccine and syringe provide the normal levels of protection by a result in which control mice are killed, whereas mice immunised with either fresh vaccine or the stabilised vaccine survive the challenge.

STATEMENTS OF INVENTION

The following numbered statements set out aspects of the invention and form part of the description.
1. A pharmaceutical syringe comprising a pharmaceutical material stabilised in a soluble dry glass coating the surfaces of the voids in a compressible porous matrix which is located within the barrel of the syringe between the plunger and the needle fitting.
2. A pharmaceutical syringe according to statement 1 characterised in that the porous matrix is compressible.
3. A pharmaceutical syringe according to state en or 2 characterised in that the porous matrix is a sponge.
4. A pharmaceutical syringe according to statement 1 or 2 characterised in that the porous matrix is a fibrous body.
5. A pharmaceutical syringe according to statement 2, 3, or 4 characterised in that the porous body is formed from a natural material
6. A pharmaceutical syringe according to statement 2, 3 and/or 4 characterised in that the porous matrix is formed from a synthetic plastics material.
7. A pharmaceutical syringe according to statement 5 characterised in that the porous body is formed from a natural sponge.
8. A pharmaceutical syringe according to statement 2, 3 and/or 4 characterised in that the porous matrix is formed from cellulose, polyethylene, polypropylene, polyester, polyether polyurethane, polyvinyl acetate or melamine formaldehyde resin.
9. A pharmaceutical syringe according to statements 2, 3, 4, 5, 6, 7 or 8 characterised in that the porous matrix has a functional pore size of between 1 micron and 2 mm.
10. A pharmaceutical syringe according to statements 2, 3, 4, 5, 6, 7 or 8 characterised in that the porous matrix has a functional pore size of between 10 microns and 1 mm.
11. A pharmaceutical syringe according to statements 2, 3, 4, 5, 6, 7 or 8 characterised in that the porous matrix has a functional pore size of between 10 microns and 100 microns.
12. A pharmaceutical syringe according to statement 4 characterised in that the glassy substances forms a coating on the surface of the fibres or pores thus defining spaces allowing the liquid to pass through.
13. A pharmaceutical syringe according to statement 1 characterised in that the carrier liquid is aqueous.
14. A pharmaceutical syringe according to statement 1 characterised in that the carrier liquid is an organic solvent.
15. A pharmaceutical syringe according to any previous statement characterised in that the porous matrix is treated with a blocking agent.
16. A pharmaceutical syringe according to any previous statement characterised in that the porous matrix is treated with a surfactant.
17. A pharmaceutical syringe according to statement 1 characterised in that the porous matrix is hydrophilic for the application of water soluble glassy substances and hydrophobic for the application of oil soluble glassy substances.
18. A pharmaceutical syringe according to any previous statement characterised in that the glass is an amino acid glass, a sugar glass, a hydrophobically modified sugar glass, a carbohydrate glass, or mixtures thereof the syringe being for the administration of a liquid-carried pharmaceutical to a patient characterised by an active pharmaceutical material stabilized in a glassy material that is soluble in the liquid and that forms a coating on supporting means located in the passage so that the glassy material will dissolve in the liquid thereby releasing the pharmaceutical into the liquid.
19. A method of storing and or transporting a biological agent stabilized in a glassy substance soluble in a carrier liquid characterised in that the biological agent is stored in a compressible porous supporting structure in a passage for the flow of the said liquid so that, the agent can be administered by aspirating the carrier liquid into the spaces or pores of the supporting structure and then causing the liquid to be expelled through the passage and thence to the patient as the porous supporting structure is compressed.
20. A method of preparing a pharmaceutical prior to administration to a patient in which a carrier liquid is caused to flow along a passage containing an active ingredient stabilised by a glassy substance so that the agent becomes dissolved or dispersed in the liquid prior to delivery to the patient.

21. A pharmaceutical syringe defining a spongy or fibrous body and glassy material stabilising an active ingredient deposited on the pores of the porous matrix or the fibres of the fibrous body, the coated pores or fibres defining spaces between them whereby a solvent can pass through the matrix dissolving the glassy substance.

The invention claimed is:

1. A pharmaceutical syringe comprising a syringe barrel comprising an interior syringe barrel wall, a proximal opening configured to receive a plunger in contact with the interior syringe barrel wall, and an integrally formed outlet connectable to a needle, the syringe barrel containing a compressible porous matrix, wherein the compressible porous matrix contains a pharmaceutical suitable for administration into a human patient and wherein the pharmaceutical is in a soluble glass in the compressible porous matrix.

2. The pharmaceutical syringe according to claim 1, wherein the compressible porous matrix in a non-compressed state occupies at least about 10% of a volume of the syringe barrel.

3. The pharmaceutical syringe according to claim 1, wherein the compressible porous matrix has a compressibility of about 2:1 or more.

4. The pharmaceutical syringe according to claim 1, wherein a gap for a passage of air during venting of the syringe is present between the compressible porous matrix and the interior syringe barrel wall.

5. The pharmaceutical syringe according to claim 1, wherein the compressible porous matrix is in the form of an elongate block.

6. The pharmaceutical syringe according to claim 1, wherein the compressible porous matrix is in a form of a block having a non-circular cross section.

7. The pharmaceutical syringe according to claim 6 wherein the block has a rectangular cross section.

8. The pharmaceutical syringe according to claim 1, wherein the compressible porous matrix is a foam, a sponge, or a fibrous body.

9. The pharmaceutical syringe according to claim 8, wherein the compressible porous matrix is cellulose foam, polyurethane foam, or melamine foam.

10. The pharmaceutical syringe according to claim 1, wherein the compressible porous matrix has a functional pore size of between:
a) 1 micron and 2 mm;
b) 10 micron and 1 mm; or
c) 10 micron and 100 micron.

11. The pharmaceutical syringe according claim 1, wherein the compressible porous matrix is hydrophilic for an application of water soluble glassy substances.

12. The pharmaceutical syringe according to claim 1, wherein the compressible porous matrix is hydrophobic for an application of oil soluble glassy substances.

13. The pharmaceutical syringe according to claim 1, wherein the pharmaceutical is stabilized in the soluble glass on the compressible porous matrix.

14. The pharmaceutical syringe according to claim 1, wherein the soluble glass is an amino acid glass, a sugar glass, a hydrophobically modified sugar glass, a carbohydrate glass, or a mixture thereof.

15. The pharmaceutical syringe according to claim 14 wherein the soluable glass is a trehalose glass.

16. The pharmaceutical syringe according to claim 1, wherein the compressible porous matrix is fixed to a seal of a syringe plunger.

17. The pharmaceutical syringe according to claim 1 wherein the outlet is directly connectable to the needle.

18. The pharmaceutical syringe according to claim 1 further comprising the plunger slideably housed within the barrel, wherein the compressible porous matrix is located between the plunger and the outlet such that partial withdrawal of the plunger to aspirate a carrier liquid into the barrel rehydrates the compressible porous matrix such that the soluble glass containing the pharmaceutical dissolves.

19. The pharmaceutical syringe according to claim 18 wherein movement of the plunger to discharge the carrier liquid in the barrel results in compression of the compressible porous matrix.

20. The pharmaceutical syringe according to claim 19 wherein, when the plunger is fully depressed towards the outlet, the compressible porous matrix is compressed and the carrier liquid in the compressible porous matrix is expelled therefrom and exits the syringe via the outlet.

21. A method of producing a compressible porous matrix insert comprising
  contacting a compressible porous matrix with a solution of a glass-forming material, which solution contains a pharmaceutical for delivery into a patient, and
  drying the solution to form a glass in the compressible porous matrix, which glass comprises the pharmaceutical, wherein the compressible porous matrix is capable of being placed into a barrel of a pharmaceutical syringe comprising a syringe barrel comprising an interior syringe barrel wall, a proximal opening configured to receive a plunger in contact with the interior syringe barrel wall, and an integrally formed outlet at a distal end of the syringe barrel connectable to a needle.

22. The method according to claim 21, comprising treating the compressible porous matrix with a blocking agent before contacting the compressible porous matrix with the solution of glass-forming material containing the pharmaceutical.

23. The method according to claim 21 comprising treating the compressible porous matrix with a surfactant.

* * * * *